(12) United States Patent
Geisser et al.

(10) Patent No.: US 9,101,265 B2
(45) Date of Patent: Aug. 11, 2015

(54) ADAPTER DEVICE TO COUPLE AN ENDOSCOPE WITH A MEDICAL APPLIANCE

(75) Inventors: Romana Geisser, Blumberg (DE); Fritz Hensler, Neuhausen (DE)

(73) Assignee: KARL STORZ GMBH & CO. KG (DE)

( * ) Notice: Subject to any disclaimer, the term of this patent is extended or adjusted under 35 U.S.C. 154(b) by 787 days.

(21) Appl. No.: 12/956,858

(22) Filed: Nov. 30, 2010

(65) Prior Publication Data

US 2011/0130631 A1 Jun. 2, 2011

(30) Foreign Application Priority Data

Nov. 30, 2009 (DE) .................. 10 2009 056 107

(51) Int. Cl.
| | | |
|---|---|---|
| A61B 1/04 | (2006.01) | |
| A61B 1/06 | (2006.01) | |
| H04N 9/47 | (2006.01) | |
| H04N 7/18 | (2006.01) | |
| F16L 27/00 | (2006.01) | |
| H01R 13/62 | (2006.01) | |
| A61B 1/00 | (2006.01) | |
| A61B 1/07 | (2006.01) | |
| G02B 23/24 | (2006.01) | |

(52) U.S. Cl.
CPC ........... *A61B 1/00128* (2013.01); *A61B 1/0669* (2013.01); *A61B 1/07* (2013.01); *G02B 23/2476* (2013.01); *A61B 1/00126* (2013.01)

(58) Field of Classification Search
USPC ................. 600/109–112, 127, 129, 132, 175; 285/144.1–154.1; 439/299, 300, 439/306–310, 320–323; 362/574
See application file for complete search history.

(56) References Cited

U.S. PATENT DOCUMENTS

| | | | | |
|---|---|---|---|---|
| 4,288,110 | A | * | 9/1981 | Grenell ..................... 285/148.13 |
| 4,414,608 | A | * | 11/1983 | Furihata ........................ 362/574 |
| 4,576,144 | A | | 3/1986 | Ishii |
| 4,601,284 | A | * | 7/1986 | Arakawa et al. .............. 600/112 |
| 2004/0108721 | A1 | * | 6/2004 | Olson ........................... 285/357 |
| 2006/0069307 | A1 | * | 3/2006 | Boulais ........................ 600/132 |
| 2009/0116260 | A1 | | 5/2009 | Rovegno | |

FOREIGN PATENT DOCUMENTS

DE 1987245 U 6/1968

OTHER PUBLICATIONS

Storz Brochure; Karl Storz—Endoskope—The Diamond Standard; "Der Karl Storz Tele Pack Kompakt, Transportabel, Universell"; www.karlstroz.com; Aug. 2009; 12 pages.

(Continued)

*Primary Examiner* — Ryan Henderson
(74) *Attorney, Agent, or Firm* — Whitmyer IP Group LLC (57) ABSTRACT

An adapter device, which is configured to couple an endoscope with a medical appliance, such that the medical appliance is provided to generate light to illuminate an object to be investigated by an endoscope, includes an adapter body with a through-hole through which light generated by the medical appliance can be transmitted, and a fastening device to removably secure the adapter body on the medical appliance. The side of the adapter body that is to face the medical appliance is configured to be held form-locked in a predetermined angle position when the adapter body is secured on the medical appliance.

19 Claims, 4 Drawing Sheets

(56) References Cited

OTHER PUBLICATIONS

Storz Brochure; Karl Storz GmbH & Co. KG; Karl Storz—Endoskope Industrial Group; "Techno Pack X mit Multipoint-Messsystem"; www.karlstorz.com; Nov. 2006; 2 pages.

Karl Storz Product Flyer: "Kompact Leicht Portable Pack Digital"; published in Aug. 2010; 3 pages.

Karl Storz Product Flyer: "Techno Pack (tm)—Die Mobile Lösung"; published in 2000; 2 pages.

* cited by examiner

ADAPTER DEVICE TO COUPLE AN ENDOSCOPE WITH A MEDICAL APPLIANCE

CROSS-REFERENCE TO RELATED APPLICATIONS

The present application claims priority of German patent application No. 10 2009 056 107.2 filed on Nov. 30, 2009, the content of which is incorporated herein by reference.

FIELD OF THE INVENTION

The present invention relates to an adapter device to couple an endoscope with a medical appliance, where the medical appliance is configured to generate light to illuminate an object that is to be investigated by means of an endoscope and on a medical appliance.

BACKGROUND OF THE INVENTION

In medical (human and veterinarian medical) and non-medical, technical applications of an endoscope, as a rule a light source is required to illuminate the observed body cavity. The light source is, for example, a halogen incandescent lamp or a xenon high-pressure gas-discharge lamp. The light source together with devices for power supply, control or regulation and a user interface is positioned in a housing. A proximal end of an endoscope can be coupled with the medical appliance by a flexible light conductor cable or directly. Light generated by the light source, in some cases by means of the flexible light conductor cable, is transmitted or conducted to the proximal end of the endoscope and by means of one or more light wave conductors from the proximal end to the distal end of the endoscope.

The couplings on the ends of a light wave conductor on the one hand and a coupling provided for direct coupling with a medical appliance on the proximal end of an endoscope are clearly of different configurations. Therefore a medical appliance must have two different couplings, depending on whether it is to be coupled with a light conductor cable or directly with a proximal end of an endoscope. For example, a medical appliance can alternatively be equipped either with a coupling for a light conductor cable or with a coupling for direct coupling with a proximal end of an endoscope. Because the coupling on the medical appliance must be precisely adjusted, an exchange of the coupling on a medical appliance with light source is possible only with their producer.

If a medical appliance is equipped with a coupling for direct coupling with a proximal end of an endoscope, if necessary a light conductor cable can be coupled with the medical appliance if necessary by means of an auxiliary adapter. This auxiliary adapter, however, clearly reduces the light yield and makes handling difficult.

An air connection is often required to connect an endoscope; it can take the form in particular of a videoscope, bronchoscope or the like. Thus an adapter must also be provided, which will have an air connection available to ensure the preparation of air or another fluid.

SUMMARY OF THE INVENTION

An object of the present invention consists in making possible an improved coupling of a medical appliance with integrated light source with an endoscope, for example a video scope or bronchoscope, alternatively either directly or via a light conductor cable.

This object is achieved through the statements in the independent claims.

Refinements are indicated in the dependent claims.

Embodiments of the present invention are based on the idea of configuring adapter devices for coupling an endoscope with a medical appliance and a coupling device on a medical appliance in such a way that an adapter device fastened on the medical appliance is held form-locked in a position at a predetermined angle in relation to the coupling device. For this purpose the adapter device comprises a recess and the coupling device has a convex device and/or the coupling device on the medical appliance has a recess and the adapter device has a convex device, so that the recess and the convex device are configured in such a way that the convex device can engage in the recess with little free play. The convex device can be, for example, a spike or pin, while the recess can be a borehole.

An advantage of the form-locked connection for the adapter device in a predetermined angle position relatively to the coupling device on the medical appliance consists in the fact that the adapter device can be replaced without adjustment being necessary. Replacement of the adapter device can thus be undertaken by a technical layperson without disadvantageous consequences for the optical coupling between the endoscope and the medical appliance. As a result, considerable costs can be spared for sending the medical device to the producer for replacement and adjustment of the adapter device by the producer, and for shipping the medical appliance back to the owner. Besides these costs, there is a saving in terms of the corresponding downtime of the medical appliance. While the appliance is unavailable to the owner for at least a few days in the event of a conventional replacement with subsequent adjustment by the producer, with the present invention an exchange of the adapter device is possible within a few seconds or minutes and with correspondingly minimal costs. The medical appliance is immediately available again without restriction.

In addition, it becomes possible to avoid the disadvantages of the aforementioned auxiliary adapter for coupling a light conductor cable on a coupling device, which is primarily intended and configured for direct coupling with a proximal end of the endoscope. With an exchange of the adapter device on a medical appliance that can be executed easily and quickly, an alternative and alternating possibility is the coupling of the proximal end of the endoscope on the medical appliance. The coupling in particular can be optimal since it avoids transmission losses or a reduction of the light gain through an additional adapter.

An adapter device to couple an endoscope with a medical appliance that is configured to generate light to illuminate an object to be observed by means of the endoscope includes an adapter body with a through-hole through which the light generated by the medical appliance can be transmitted, and a fastening device for removable attachment of the adapter body on the medical appliance, whereby the side of the adapter body facing the medical appliance is configured to be held in form-locked connection in position at a predetermined angle when the adapter body is attached on the medical appliance.

With such an adapter device, on the side of the adapter body that is to face the medical appliance, it is possible to provide a borehole or other recess that is configured so that a convex device engages in the recess on the medical appliance. A convex device on the medical appliance can be, for example, a dome, pin, nub or stud. Instead of a single recess on the adapter device and a single convex device on the medical appliance, several recesses can be configured on the adapter device and several convex devices on the medical appliance to engage with one another in pairs and to establish, in a form-locked linkage, a predetermined angle position of the adapter body to the medical appliance.

With an adapter device as described here, the fastening device can include a fastening screw-on sheath with an outer thread that can rotate with respect to the adapter body but can slide axially only within an interval that is restricted at least in the proximal direction. Said interval, in particular, is restricted in both directions and constitutes the axial play of the fastening screw-on sheath with respect to the adapter body. Alternatively the fastening screw-on sheath can be secured on the adapter body without axial play. The outer thread is, in particular, a thread with multiple turns, for example a triple-turn thread. Specifically, a triple-turn thread, on the one hand, depending on the selected length of the thread, can be mounted with only one or a few rotations (even with less than one rotation) and therefore rapidly, while offering, on the other hand, a sufficient security against accidental release of the screw-in connection. Instead of an outer thread or in addition to it, the fastening screw-on sheath can comprise an inner thread and/or a bayonet coupling for releasable mechanical coupling with the medical appliance. The adapter device, in addition, can comprise a screw-nut that is or can be screwed onto the portion of the adapter body that is to face the medical appliance, in order to hold the fastening screw-on sheath on the adapter body or to restrict in the proximal direction the aforementioned interval of axial mobility.

A fastening screw-on sheath can comprise a fastening device that is especially cost-effective to produce and at the same time is robust and reliable. A fastening screw-on sheath can be configured in such a way that it can also be operated intuitively by technically non-practiced medial personnel and thus quickly and reliably without time-intensive training.

A three-part structure of the adapter device, consisting of adapter body, fastening screw-on sheath and a screw-nut that secures the fastening screw-on thread on the adapter body, can offer a particularly useful combination of low production costs, mechanical robustness, and precision. The adapter body, the fastening screw-on sheath and the screw-nut, in particular, can each be manufactured of stainless steel or another metallic or non-metallic material in simple manner by turning, milling and boring.

An adapter device as described here, in addition, can comprise a marker on the side of the adapter body facing the endoscope to indicate a foreseen angle position of the adapter body with respect to the medical appliance. Such a marking can simplify insertion and securing of the adapter body on a medical appliance.

An adapter device as described here can be configured to provide a coupling on a proximal end of an endoscope.

In case of immediate coupling with an endoscope, the medical appliance can include a fluid connection nipple to pump air or another fluid through the endoscope to its distal end or to suction it out from there. For optimal compatibility with a medical appliance of this configuration, an adapter device, which is configured to produce a coupling on a proximal end of an endoscope, can include a fluid connection borehole in the form of an additional through-hole to receive a fluid connection nipple of the medical appliance and a fluid connection nipple for the coupling of an endoscope. A fluid connection between the medical appliance and the endoscope can be formed via the fluid connection borehole.

With an adapter device as described here, the through-hole can be configured to insert a proximal end of a coupling of a light conductor cable. If the adapter device for a medical appliance is configured with a fluid connection nipple, it can include a blind hole on the side that is to face the medical appliance to insert the fluid connection nipple. Said blind hole can be configured not to be immediately contiguous with the fluid connection nipple but instead to make possible a streaming of fluid through the fluid connection nipple and between the outer surface of the fluid connection nipple and the inner surface of the blind hole.

An adapter set includes an adapter device in which the through-hole as described above is configured to insert a proximal end of a coupling of a light conductor cable and an adapter device as described above is configured to insert a coupling on a proximal end of an endoscope. The adapter devices of the adapter set, alternatively, can be secured on a medical appliance. Because of the form-locked securing of a predetermined angle position of the adapter body with respect to the medical appliance, the adapter devices can be exchanged with one another simply without requiring an adjustment and thus quickly. While one of the two adapter devices makes possible an optimal direct coupling between a medical appliance and an endoscope, the other allows an optimal coupling of the medical appliance and the endoscope via a light conductor cable or only the coupling of the medical appliance with a light conductor cable. The coupling here is optimal, in particular with respect to low light losses or a high transmission and/or with respect to convenience of operation.

A medical appliance includes a housing, a light source positioned in the housing to generate light to illuminate a site that is to be investigated with an endoscope, and a coupling device to couple a proximal end of an endoscope via an adapter device onto the medical appliance either directly or via a light conductor cable, and to transmit light from the light source to the endoscope, such that the coupling device is configured to secure an adapter body of an adapter device in form-locked connection in a predetermined angle position when the adapter body is secured to the light source. The medical appliance is configured to be connected with one of the adapter devices described above.

BRIEF DESCRIPTION OF THE DRAWINGS

Embodiments are described in further detail hereinafter with reference to the appended drawings

DETAILED DESCRIPTION OF THE INVENTION

Figure 1:
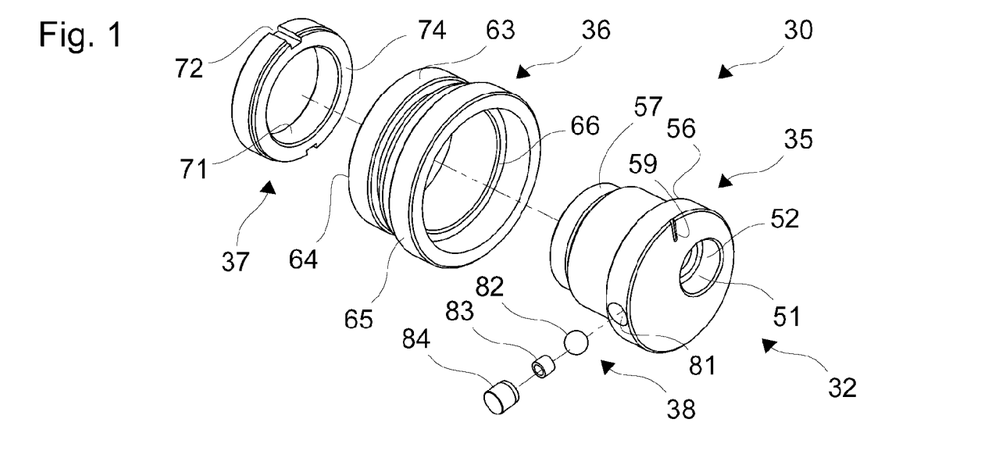
FIG. 1 is a schematic axonometric depiction of components of a first adapter device.
Figure 2:
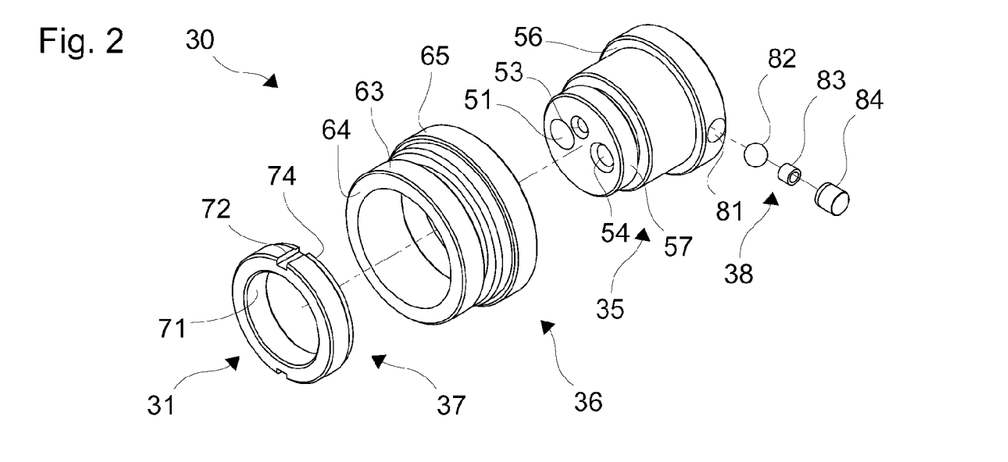
FIG. 2 is another schematic axonometric depiction of the components of the first adapter device.
Figure 3:
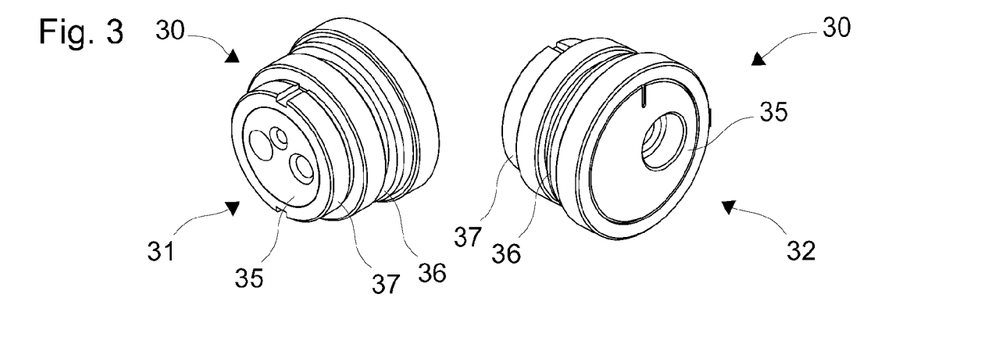
FIG. 3 is a schematic axonometric depiction of the first adapter device.
Figure 4:
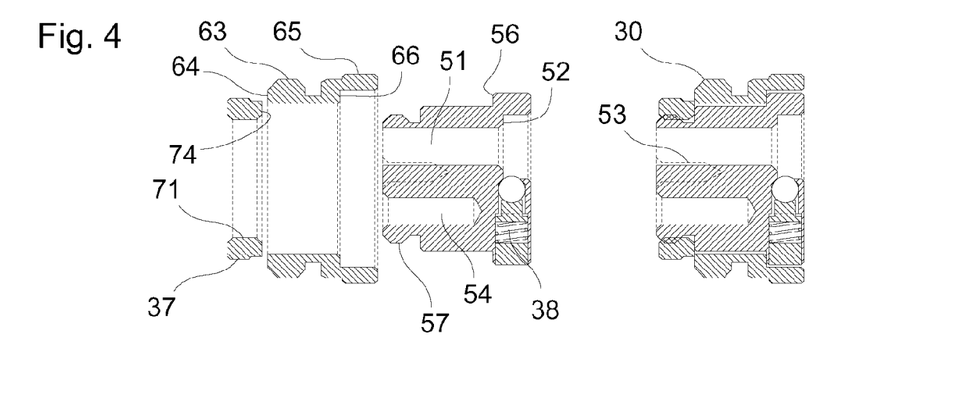
FIG. 4 presents schematic sectioned depictions of the first adapter device.

FIGS. 1 through 3 show schematic axonometric depictions of the components of a first adapter device or of the assembled first adapter device. FIG. 4 shows schematic sectioned depictions of the first adapter device. At the left in FIG. 4, the three main components of the first adapter device are shown separately, similarly as in FIGS. 1 and 2, and at the right the first adapter device is shown assembled or installed. The illustrated section planes each contain the longitudinal axis of the adapter device.

The first adapter device 30 comprises a side that is to face a medical appliance or a proximal side 31 (compare FIG. 2 and FIG. 3, right) and a side that is to face a light conductor cable or an endoscope or a distal side 32 (compare FIG. 1 and FIG. 3, right). The first adapter device 30 includes an adapter body 35, a fastening screw-on sheath 36, and a screw-nut 37. A catch-lock device 38 is integrated into the adapter body 35. The adapter body 35, fastening screw-on sheath 36, and a screw-nut 37 are each partly rotationally symmetrical to an axis that extends from the proximal side 31 to the distal side 32. The rotational symmetry of the adapter body 35, fastening screw-on sheath 36, and screw-nut 37, however, is interrupted by several elements in each case, for example by boreholes and threads.

The adapter body 35 comprises a through-hole 51 with a ring-shaped recess 52. As can be seen in particular from FIG. 4, the through-hole 51 is positioned essentially parallel to the longitudinal axis of the first adapter device 30. The through-hole 51 comprises two essentially cylindrical segments, between which the ring-shaped recess 52 is positioned.

In addition the adapter body 35 comprises a first blind hole 53, which extends from the proximal side outward into the adapter body 35. The contour of the first blind hole 53 is shown in broken lines in FIG. 4 because it is situated outside the illustrated section plane. The first blind hole 53 comprises an essentially cylindrical segment. At the entrance of the first blind hole 53 on the proximal side 31 of the adapter body 35, the first blind hole 53 comprises a spherical or conical segment.

The adapter body 35 comprises, in addition, a second blind hole 54, which is positioned essentially parallel to the longitudinal axis of the first adapter device 30. The second blind hole 54 is essentially cylindrical, with a spherical or conical segment at the entrance of the proximal side 31 of the adapter body 35.

The adapter body 35 of the first adapter device 30 also comprises a ring-shaped recess 56 close to the distal end of the adapter body 35 and an outer thread 57 close to the proximal end of the adapter body 35.

The fastening screw-on sheath 36 of the first adapter device 30 comprises close to its proximal end an outer thread 63 and a proximal front surface 64. The outer thread is in particular a multiple-turn thread, for example a triple-turn thread, to make screw attachment possible with one turn or fewer turns or less than one turn. Close to the distal end the fastening screw-on sheath 36 comprises on its outer surface a ring-shaped ribbed gripping surface 65. In addition, the fastening screw-on sheath 36 comprises a ring-shaped recess 66 between two cylindrical segments of its inner surface.

The screw-nut 37 comprises an inner thread 71 that can be screwed in complementary manner or with the outer thread 57 onto the adapter body 35. On its outer periphery the screw-nut 37 comprises one or more grooves 72 positioned essentially parallel to the longitudinal axis of the first adapter device 30. A rotary moment can be transmitted onto the screw-nut 37 via the grooves 72 with an appropriate tool to screw the screw-nut onto the outer thread 57 of the adapter body 35 and to tense it with said body in order to prevent accidental loosening of the screw-nut 37. Accidental loosening of the screw-nut 37 from the adapter body, in addition, can be prevented through one or more soldering points, by welding, cementing, use of a splint or other actions. In addition the screw-nut 37 comprises a front surface 74.

The catch-lock device 38 includes a transverse borehole 81, close to the distal side 32 of the adapter body 35, extending from an outer mantle surface of the adapter body 35 to the through-hole 51. In addition, the catch-lock device 38 includes a sphere 82, a coil spring 83 and a dowel. The depiction in FIG. 4 shows a variant in which a piston is positioned between the sphere 82 and the coil spring 83. The transverse borehole 81, on its end bordering on the through-hole 51, has a reduced cross-section, so that the sphere 82 and transverse borehole 81 can enter or extend only partway into the through-hole 51.

The coil spring 83 is partly compressed between the sphere 82 and the dowel 84 in the transverse borehole 81, so that the sphere 82 is pre-tensed in the direction into the through-hole 51, but can be forced completely out of the cross-section of the through-hole 51 by a sufficient force.

In particular at the right in FIG. 4 it can be recognized that, with the first adapter device 30 in installed or assembled position, an axial movement of the fastening screw-on sheath 36 in the distal direction is restricted by the contiguity of the ring-shaped recess 66 of the fastening screw-on sheath 36 to the ring-shaped recess 56 on the adapter body 35. It an also be seen that an axial movement of the fastening screw-on sheath 36 in the proximal direction is restricted by a contiguity of the proximal front surface 64 of the fastening screw-on sheath 36 on the one hand and of the distal front surface 74 of the screw-nut 37 on the other hand, which partially overlap with one another.

At the right in FIG. 4, in addition, it can be seen that the adapter body 35, fastening screw-on sheath 36 and screw-nut 37 of the first adapter device 30 are of such dimensions that the fastening screw-on sheath 36 is secured with little or no free play in the axial direction between the ring-shaped recess 56 on the adapter body 35 on the one hand and the distal front surface 74 of the screw-nut 37, which is entirely screwed onto the adapter body 35, on the other hand. The fastening screw-on sheath 36, however, can rotate freely around the longitudinal axis of the first adapter device 30.

Figure 5:
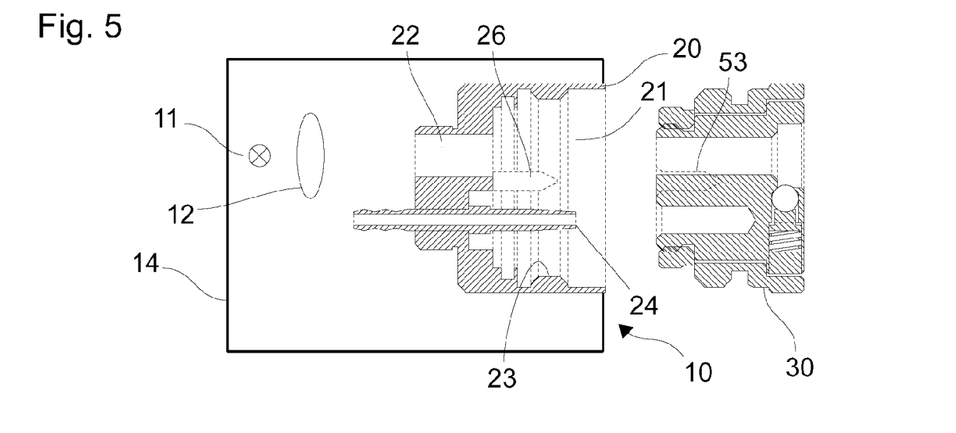
FIG. 5 is a schematic sectioned depiction of a medical appliance and of the first adapter device.
Figure 6:
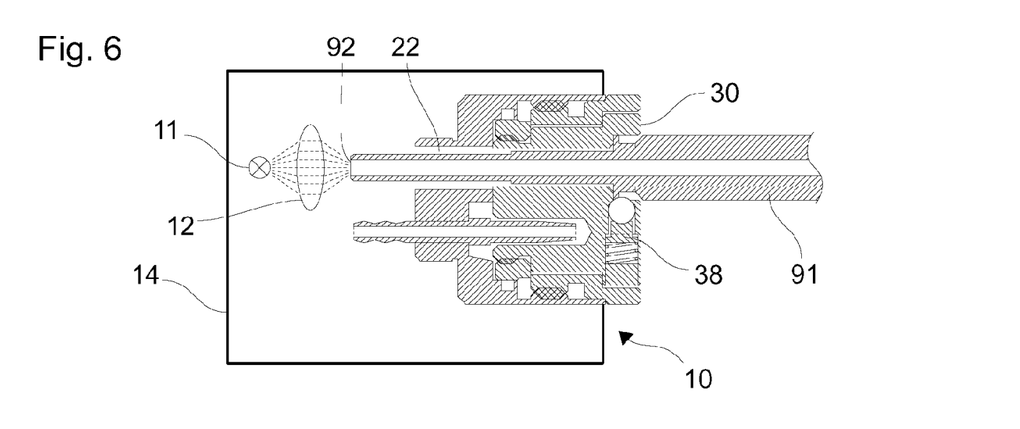
FIG. 6 is another schematic sectioned depiction of the medical appliance and of the first adapter device.

FIGS. 5 and 6 show schematic sectioned depictions of a medical appliance 10 with a light source 11 and a lens 12 in a housing 14. A coupling device 20 with a recess 21 is positioned in an opening of the housing 14. Said recess 21 is essentially rotation-symmetric and adapted to the outer shape of the first adapter device 30. A through-hole 22 in the coupling device 20 extends from the recess 21 in the direction toward the lens 12 and light source 11. Positioned on the wall of the recess 21 is an inner thread 23, which can be screwed complementarily to the outer thread 63 of the fastening screw-on sheath 36 of the first adapter device 30 or with it.

A fluid connection nipple 24 and a pin or mandrel 26 extend into the recess 21. The contour of the mandrel 26 is illustrated with an interrupted line because the mandrel 26 lies outside the section plane shown in FIG. 5. Contrary to the depiction in FIGS. 5 and 6, one end of the fluid connection nipple 24, which is turned away from the recess 21, can end or continue in a tube, which takes another direction, for example at a right angle to the fluid connection nipple 24.

Not shown in FIGS. 5 and 6 are additional devices of the medical appliance 10, for example devices for power supply, control or adjustment of the light source 11, a user interface, a pump or blower, either of which is connected with the fluid connection nipple 24.

It can be recognized in FIG. 6 that the first adapter device 30 can be inserted partially into the recess 21 of the coupling device 20. In the process, the outer thread 63 on the fastening screw-on sheath 36 and the inner thread 23 on the coupling device 20 engage with one another or are screwed together with one another. In addition, the mandrel 26 engages in the first blind hole 53 in the adapter body 35. Because of a precise fit or the smallest possible free play between the mandrel 26 on the coupling device 20 on the one hand and the first blind hole 53 on the other hand, the first adapter device 30 is held in a predetermined angle position with respect to the coupling device 20.

It can also be seen in FIG. 6 that the fluid connection nipple 24 of the coupling device 20 engages in the second blind hole 54. Between the outer wall of the fluid connection nipple 24 on the one hand and the inner wall of the second blind hole 54 on the other hand, there remains a gap through which a fluid coming through the fluid connection nipple 24 can flow. The result is a reduction in the build-up of excess or low pressure in the fluid connection nipple 24 and the connected components when the first adapter device 30 is in operation. This also prevents any backed-up pressure in the medical appliance and the pump installed in it.

With the corresponding precise fit or low free play between the fluid connection nipple 24 and the second blind hole 54, the fluid connection nipple 24 and the second blind hole 54 can assume the function of the form-locked securing of the first adapter device 30 in a predetermined angle position with respect to the coupling device 20. In this case the mandrel 26 and first blind hole 53 are dispensed with. This is subject to the condition that the fluid connection nipple and the connection for the light conductor are asymmetrical to one another.

Illustrated in FIG. 6 is a coupling 91 on the proximal end of a light conductor cable that is inserted into the through-hole 51 in the adapter body 35 and into the through-hole 22 of the coupling device. In this way the catch-lock device 38 secures the coupling 91 in the predetermined axial position. Because of the form-locked securing of the angle position of the first adapter device 30 with respect to the coupling device 20, the coupling 91 and a light-admitting window 92 are aligned precisely on the proximal end of the coupling 91 opposite the light source 11 and the lens 12 to ensure the most complete possible coupling of the light of the light source 11 into the light conductor cable.

Figure 7:
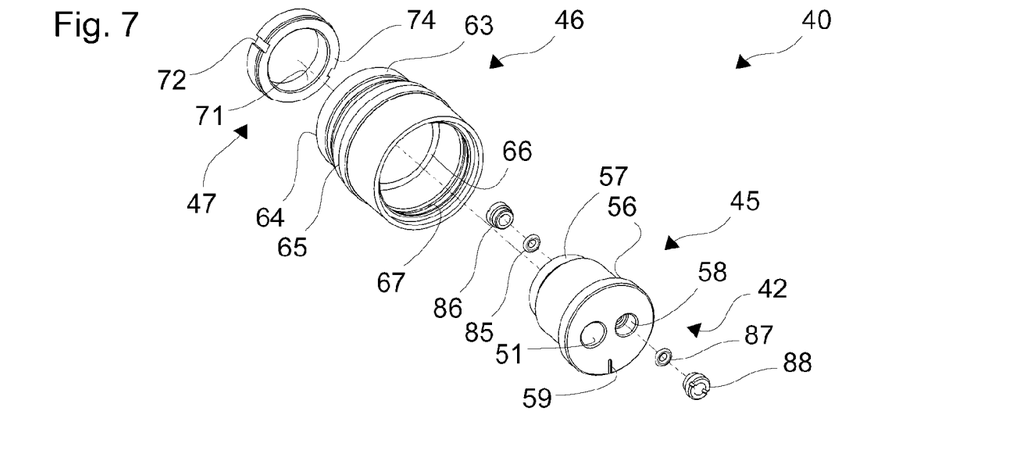
FIG. 7 is a schematic axonometric depiction of components of a second adapter device.
Figure 8:
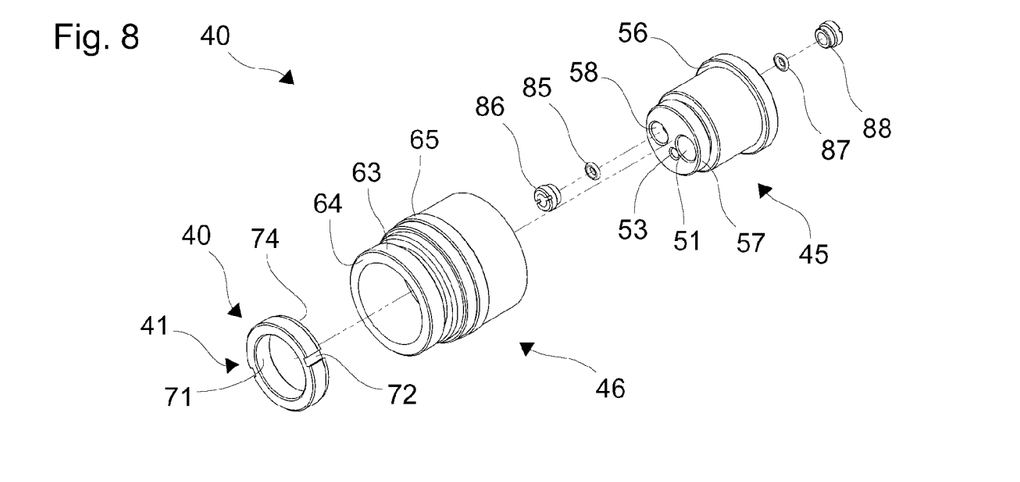
FIG. 8 is another schematic axonometric depiction of the components of the second adapter device.
Figure 9:
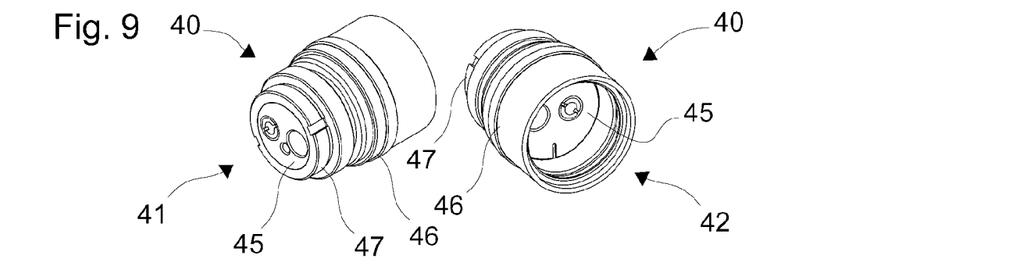
FIG. 9 presents schematic axonometric depictions of the second adapter device.
Figure 10:
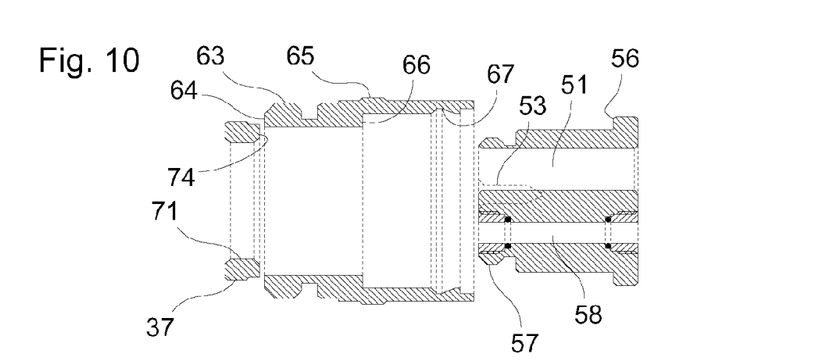
FIG. 10 is a schematic sectioned depiction of the second adapter device.

FIGS. 7 through 9 show schematic axonometric depictions of the components of a second adapter device or of the assembled second adapter device. FIG. 10 shows a schematic sectioned depiction of the three main components of the second adapter device. It is further described below, with reference to FIGS. 11 and 12, that the second adapter device is intended and configured to be applied on the same medical appliance, like the first adapter device described above with reference to FIGS. 1 through 6. Contrary to the first adapter device described above, the second adapter device, however, is not intended to be coupled with a coupling on one end of a light conductor cable. Instead, the second adapter device is intended and configured to be coupled directly with one proximal end of an endoscope. This is the reason for the differences, described hereinafter, between the second adapter device and the first adapter device.

The second adapter device 40 comprises a side that is to face a medical appliance or proximal side 41 (compare FIG. 7 and FIG. 9, left) and a side that is to face a light conductor cable or an endoscope or distal side 42 (compare FIG. 7 and FIG. 9, right). Similarly as in the first adapter device 30 described above, the second adapter device 40 includes an adapter body 45, a fastening screw-on sheath 46 and a screw-nut 47, which however differ in part from the corresponding components in the first adapter device. The adapter body 45, the fastening screw-on sheath 46 and the screw-nut 47 are each partly rotation-symmetrical to an axis that extends from the proximal side 41 to the distal side 42. The rotation symmetry of the adapter body 45, fastening screw-on sheath 46 and screw-nut 47 is, however, interrupted by several elements, for example by boreholes and threads.

Described below are only those properties of the components of the second adapter device 40 by which the second adapter device 40 is distinguished from the first adapter device 30. Those properties of the components of the second adapter device 40 not mentioned below correspond to the properties of the first adapter device 30.

The adapter body 45 comprises a through-hole 51 with a cross-section that remains constant from the proximal side 41 to the distal side 42. The through-hole 51 is positioned essentially parallel to the longitudinal axis of the second adapter device 40. In addition the adapter body 45 comprises a first blind hole 53, which corresponds in terms of its position, size and shape to the blind hole in the adapter body of the first adapter device 30.

Instead of a second blind hole, the adapter body 45 comprises a fluid connection borehole 58 in the form of a through-hole that is positioned essentially parallel to the longitudinal axis of the second adapter device 40. The fluid connection borehole 58 comprises on its proximal side 41 and on the distal side 42 one area each with a step-shaped broadened cross-section. Inserted in these two areas are a first O-ring 85 and a first threaded bushing 86 or a second O-ring 87 and a second threaded bushing 88. Apart from the elastic O-rings 85, 87, which protrude somewhat into the cross-section of the fluid connection borehole 58, the result is a channel with an essentially constant cross-section from the proximal side 41 to the distal side 42 of the adapter body 45 or of the second adapter device 40.

Contrary to the fastening screw-on sheath 36 of the first adapter device 30, the fastening screw-on sheath 46 of the second adapter device 40, with the second adapter device 40 in installed or assembled position, extends beyond the adapter body 45 on the distal side 42. In addition, the fastening screw-on sheath 46, in the area in which it extends beyond the adapter body 45, comprises a ring-shaped groove 67 on the inside close to its distal border. The function of this groove is described more fully below with reference to FIG. 12.

Figure 11:
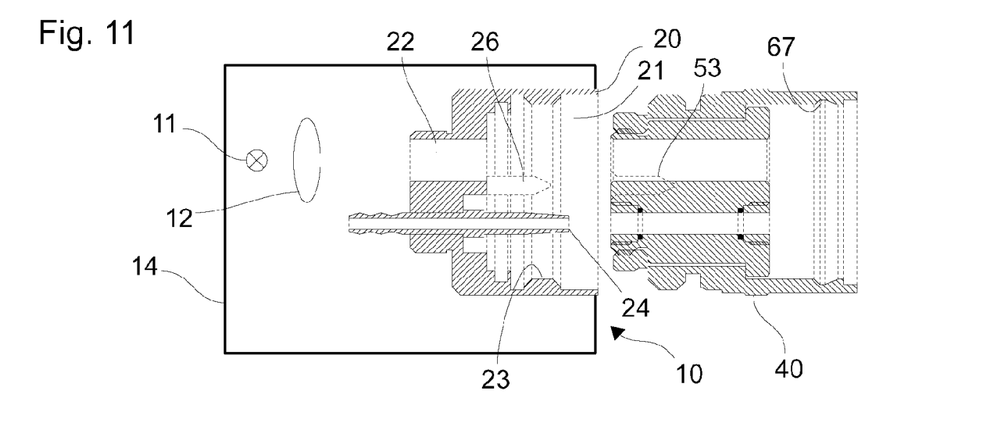
FIG. 11 is a schematic sectioned depiction of the medical appliance from FIGS. 5 and 6 and of the second adapter device.
Figure 12:
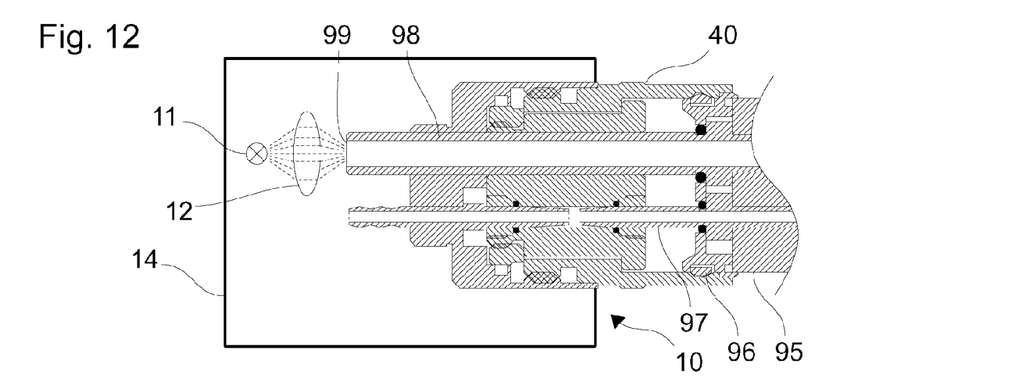
FIG. 12 is a schematic sectioned depiction of the medical appliance from FIGS. 5, 6 and 11 and of the second adapter device.

FIGS. 11 and 12 show schematic sectioned depictions of the medical appliance 10 already described above with reference to FIGS. 5 and 6 and of the second adapter device 40. In FIG. 11 the second adapter device 40 is aligned with respect to the coupling device 20 on the medical appliance 10, but is not yet inserted into said device. FIG. 12 shows the second adapter device 40 inserted in the coupling device 20 on the medical appliance 10 or in its recess 21. As already explained above for the first adapter device 30 with reference to FIGS. 5 and 6, in the second adapter device 40 as well, the outer thread 63 on the fastening screw-on sheath 46 engages in the inner thread 23 of the coupling device 20. It can further be seen in FIG. 12 that the fluid connection nipple 24 of the coupling device 20 engages in the fluid connection borehole 58 coming from the proximal side 41.

The mandrel of the coupling device 20 engages in the first blind hole 53 in the adapter body 45. Because of a precise fit or the least possible free play between the mandrel 26 on the coupling device 20 on the one hand and the first blind hole 53 in the adapter body 45 on the other hand, the second adapter device 40 is secured in a predetermined angle position with respect to the coupling device 20, similarly as is shown above for the first adapter device 30 with reference to FIG. 6.

Also shown in FIG. 12 is a coupling 95 on the proximal end of an endoscope that is not depicted further in FIG. 12. The coupling 95 includes a spring washer 96 in a ring-shaped groove on the coupling 95. In the illustrated position of the coupling 95 with respect to the second adapter device 40, the spring washer 96 engages in the ring-shaped groove 67 on the fastening screw-on sheath 36. Owing to the elastic property of the spring washer 96 pre-tensed outward, the coupling 95 is held elastically form-locked on the second adapter device 40.

The coupling 95 comprises a fluid connection nipple 97 and a light conductor tube 98 with a light-admitting window 99. The fluid connection nipple 97 and light conductor tube 98 of the coupling 95 extend out in the proximal direction beyond other parts of the coupling 95.

The fluid connection nipple 97, from the distal side 42, engages in the fluid connection borehole 98 in the adapter body 45. The lumen of the fluid connection nipple 24 of the coupling device 20 and the lumen of the fluid connection nipple 97 of the coupling 95 are in connection with one another via the lumen of the fluid connection borehole 58. The elastic O-rings 85, 87 are contiguous with the outer surfaces of the fluid connection nipples 24, 97. Thereby the connection between the fluid connection nipple 24 of the coupling device 20 of the medical appliance 10 on the one hand and the fluid connection nipple 97 of the coupling 95 on the proximal end of the endoscope on the other hand are insulated from penetration by fluids from the outside.

The light conductor tube 98 engages in the through-hole 51 in the adapter body 45 and in the through-hole 22 of the coupling device 20. Because of the predetermined angle position of the adapter body 45 relative to the coupling device 20 imposed as a result of the mandrel 26 on the coupling device 20 and the blind hole 53 in the adapter body 45, the light conductor tube 98 and in particular the light-admitting window 99 of the coupling 95 are aligned precisely with respect to the light source 11 and the lens 12. As a result, an optimal optic coupling is made possible between the light source 11 and the endoscope.

The first adapter device 30 and the second adapter device 40, on the proximal side 31 or 41 and to the extent that they engage in the recess 21 in the coupling device 20, are adapted to the coupling device 20 with respect to their outer shape, the position of the first through-holes 51, the arrangement, form and dimensions of the first blind hole 53, the arrangement and dimensions of the second blind hole 54 or of the fluid connection borehole 58. Thus the aforementioned properties of the adapter devices 30, 40 are basically identical or at least similar. The adapter devices 30, 40, however, differ from one another with respect to the cross-sections of the first through-holes 51 and with respect to the configuration of the second blind hole 54 on the one hand, or of the fluid connection borehole 58 on the other hand.

What is claimed is:

1. An adapter device for coupling an endoscope with a medical appliance configured to generate light to illuminate an object, the adapter device comprising:
    an adapter body having a longitudinal axis, a blind hole on a side of the adapter body that faces the medical appliance, and a through-hole extending essentially parallel to the longitudinal axis of the adapter body through which light generated by the medical appliance can be transmitted;
    a fastening device for removably securing the adapter body to the medical appliance, said fastening device including a fastening screw-on sheath with an outer thread that can rotate with respect to the adapter body but can slide axially only within an interval that is restricted at least in a proximal direction; and
    a screw-nut that is screwed or is to be screwed onto a portion of the adapter body that is to face the medical appliance, to secure the fastening screw-on sheath on the adapter body;
    wherein on the side of the adapter body that faces the medical appliance a borehole is provided which is configured so that a convex device on the medical appliance engages in the recess to keep the adapter body form-locked in a predetermined angle position when the adapter body is secured to the medical appliance.

2. The adapter device of claim 1, further comprising a marker on a side of the adapter body that faces the endoscope, to indicate an expected angle position of the adapter body with respect to the medical appliance.

3. The adapter device of claim 1, wherein the through-hole is configured to insert a proximal end of a coupling of a light conductor cable.

4. The adapter device of claim 1, wherein the blind hole is for inserting a fluid connection nipple, of the medical appliance, when the adapter device is positioned on the medical appliance.

5. The adapter device of claim 4, wherein the blind hole is configured in such a way that on inserting the fluid connection nipple, an intermediate space is present between the fluid connection nipple and the blind hole to allow an off-flow of fluid.

6. The adapter device of claim 1, wherein the adapter device is configured to insert a coupling on a proximal end of an endoscope.

7. The adapter device of claim 6, wherein the adapter body is configured to insert a fluid connection nipple of the medical appliance and a fluid connection nipple of the coupling of the endoscope.

8. The adapter device of claim 1, further comprising a catch-lock device, the catch-lock device integrated into the adapter body.

9. The adapter device of claim 1, wherein the borehole is positioned essentially parallel to the longitudinal axis of the adapter body.

10. The adapter device of claim 9, wherein the borehole has a cross-section that is step-shaped from its proximal side to its distal side, wherein the cross-section increases from the proximal side to the distal side of the borehole.

11. The adapter device of claim 9, further comprising an O-ring and a threaded bushing inserted into the borehole.

12. The adapter device of claim 9, wherein the borehole has an essentially constant cross-section from a proximal side to a distal side of the adapter body.

13. The adapter device of claim 1, wherein the through-hole has a ring shaped recess.

14. The adapter device of claim 1, further comprising a second blind hole positioned essentially parallel to a longitudinal axis of the adapter device, the second blind hold being essentially cylindrical, with a spherical or conical segment at an entrance of a proximal side of the adapter body.

15. A medical appliance comprising:
    a housing having a light source positioned in the housing to generate light to illuminate a site that is to be investigated with an endoscope, and a coupling device positioned in an opening of the housing; and an adapter device, the adapter device inserted in a recess of the coupling device, the adapter device coupling a proximal end of an endoscope to the medical appliance to transmit light from the light source to the endoscope, the adapter device having:

an adapter body having a longitudinal axis, a blind hole on a side of the adapter body that faces the medical appliance, and a through-hole extending essentially parallel to the longitudinal axis of the adapter body through which light generated by the light source can be transmitted, a fastening device for removably securing the adapter body to the coupling device, said fastening device including a fastening screw-on sheath with an outer thread that can rotate with respect to the adapter body but can slide axially only within an interval that is restricted at least in a proximal direction, a screw-nut that is screwed or is to be screwed onto a portion of the adapter body that is to face the housing, to secure the fastening screw-on sheath on the adapter body;

wherein the coupling device is configured to keep an adapter body of the adapter device form-locked in a predetermined angle position when the adapter body is removably secured on the coupling device.

16. The medical appliance of claim 15, wherein the blind hole is for inserting a fluid connection nipple of the medical appliance when the adapter device mates with the coupling device of the housing.

17. The medical appliance of claim 16, wherein the blind hole is configured in such a way that on inserting a fluid connection nipple, an intermediate space is present between the fluid connection nipple and the blind hole to allow for off-flow of fluid.

18. An adapter device for coupling an endoscope with a medical appliance configured to generate light to illuminate an object, the adapter device comprising:

an adapter body having a longitudinal axis and a through-hole extending essentially parallel to the longitudinal axis of the adapter body through which light generated by the medical appliance can be transmitted;

a fastening device for removably securing the adapter body to the medical appliance, said fastening device including a fastening screw-on sheath with an outer thread that can rotate with respect to the adapter body but can slide axially only within an interval that is restricted at least in a proximal direction; and a screw-nut that is screwed or is to be screwed onto a portion of the adapter body that is to face the medical appliance, to secure the fastening screw-on sheath on the adapter body; and a catch-lock device, the catch-lock device integrated into the adapter body, wherein on a side of the adapter body that faces the medical appliance a borehole is provided which is configured so that a convex device on the medical appliance engages in the recess to keep the adapter body form-locked in a predetermined angle position when the adapter body is secured to the medical appliance, wherein the catch-lock device includes a transverse borehole, a sphere, a coil spring and a dowel, the sphere, the coil spring and the dowel positioned within the transverse borehole.

19. The adapter device of claim 18, wherein the sphere and the transverse borehole extend only partway into the through-hole.

* * * * *